United States Patent
Lee et al.

(10) Patent No.: US 10,176,302 B2
(45) Date of Patent: Jan. 8, 2019

(54) METHOD OF ANALYZING CHARACTERISTICS OF MOLECULAR ORBITAL THROUGH SEQUENTIAL BLOCK FORMATION AND SYSTEM USING SAME

(71) Applicant: LG CHEM, LTD., Seoul (KR)

(72) Inventors: Seungyup Lee, Daejeon (KR); Hyesung Cho, Daejeon (KR)

(73) Assignee: LG Chem, Ltd., Seoul (KR)

( * ) Notice: Subject to any disclaimer, the term of this patent is extended or adjusted under 35 U.S.C. 154(b) by 272 days.

(21) Appl. No.: 14/902,997

(22) PCT Filed: Jul. 9, 2014

(86) PCT No.: PCT/KR2014/006144
§ 371 (c)(1),
(2) Date: Jan. 5, 2016

(87) PCT Pub. No.: WO2015/005668
PCT Pub. Date: Jan. 15, 2015

(65) Prior Publication Data
US 2016/0162663 A1 Jun. 9, 2016

(30) Foreign Application Priority Data
Jul. 9, 2013 (KR) .......... 10-2013-0080511

(51) Int. Cl.
*G06F 19/00* (2018.01)

(52) U.S. Cl.
CPC ............ *G06F 19/701* (2013.01); *G06F 19/70* (2013.01)

(58) Field of Classification Search
CPC ................. G06F 19/701; G06F 19/70
(Continued)

(56) References Cited

U.S. PATENT DOCUMENTS 6,647,342 B2 * 11/2003 Iglesia ................ B01J 19/0046
422/606
2004/0103080 A1 * 5/2004 Samukawa .......... G06F 19/709
(Continued)

FOREIGN PATENT DOCUMENTS

JP 2003-256668 A 9/2003
JP 2011-173821 A 9/2011
(Continued)

OTHER PUBLICATIONS

Mireia Guell et al., "Analysis of Electron Delocalization in Aromatic Systems: Individual Molecular Orbital Contributions to Para-Delocalization Indexes," Chem. A., 2006, 110, pp. 11569-11574.
(Continued)

*Primary Examiner* — Fernando L Toledo
*Assistant Examiner* — Adam S Bowen
(74) *Attorney, Agent, or Firm* — Dentons US LLP

(57) ABSTRACT

The present invention relates to a method of analyzing the characteristics of a molecular orbital through a sequential block formation, the method including: a) selecting a targeted molecular orbital of which the characteristics are analyzed, and then using a quantum mechanics calculation to calculate the distribution of the molecular orbital; b) forming N blocks in a radial direction at the molecular center in the molecular structure of the molecule; c) calculating a molecular orbital ratio (BX(k)) associated with each block; and d) re-arranging the blocks sequentially based on the size of the molecular orbital ratio (BX(k)) to obtain a re-arranged block spectrum.

8 Claims, 3 Drawing Sheets

(58) Field of Classification Search
USPC .......................................................... 702/32
See application file for complete search history.

(56) References Cited

U.S. PATENT DOCUMENTS

| | | | | |
|---|---|---|---|---|
| 2006/0271301 A1* | 11/2006 | Takada | ................... | G06F 17/13 702/19 |
| 2007/0043545 A1* | 2/2007 | Yonezawa | ............. | G06F 19/701 703/11 |
| 2010/0082306 A1* | 4/2010 | Mills | ................... | G06F 19/701 703/2 |

FOREIGN PATENT DOCUMENTS

KR    10-2012-0085165 A    7/2012
KR         10-1200467 B1    11/2012

OTHER PUBLICATIONS

Hongkun Park et al., "Molecular-orbital decomposition of the ionization continuum for a diatomic molecule by angle- and energy-resolved photoelectron spectroscopy," American Institute of Physics, 1996, pp. 4554-4567.

\* cited by examiner

Rearranged 7 Blocks

| BL3 | BL2 | BL4 | BL1 | BL5 |
| 25.8% | 20.4% | 19.8% | 16.7% | 16.3% |

METHOD OF ANALYZING CHARACTERISTICS OF MOLECULAR ORBITAL THROUGH SEQUENTIAL BLOCK FORMATION AND SYSTEM USING SAME

This application is a National Stage Entry of International Application No. PCT/KR2014/006144, filed Jul. 9, 2014, and claims the benefit of Korean Application No. 10-2013-0080511, filed on Jul. 9, 2013, all of which are hereby incorporated by reference in their entirety for all purposes as if fully set forth herein.

TECHNICAL FIELD

The present disclosure relates to a method for analyzing molecular orbital properties, and a system using the same. More particularly, the present invention relates to a method for quantitatively analyzing molecular orbital properties, and a system using the same.

BACKGROUND ART

A molecular orbital is introduced as a concept to simulate the behavior of an electron, as expressed as the probability of finding an electron in any specific region. Hence, a molecular orbital distribution is one of the important factors that determine electrochemical properties of a material. Molecular orbitals, which account for the distributions of electrons in a specific region in a molecular structure as a probability concept, cannot be obtained experimentally, but can be constructed using quantum mechanics.

Distribution patterns of molecular orbitals in a molecular structure are numerous and complex. For example, molecular orbitals (1) may be limited to the center of an entire molecular structure, (2) may exist only on a periphery distal to the center of a molecular structure, (3) may be found at regions near and distal to the center of a molecular structure, or (4) may be distributed across the entire molecular structure, but unevenly depending on specific regions. As such, the understanding of molecular orbital distribution tendency is prerequisite for the behavior of electrons in a molecular structure. Accordingly, a quantitative method is necessary for accurately evaluating molecular orbital distribution in an intuitive manner.

To date, there are no methods of evaluating and analyzing molecular orbital information, except for qualitative methods in which diagrams are created and compared in a visual manner. At present, however, such qualitative methods are not systematically utilized for the development of materials or the evaluation of physical properties. Considering the importance of the information that molecular orbitals, which account for electron behaviors, provide, molecular orbitals, if quantitatively and systematically analyzed like other quantitatively analyzable electrochemical properties, are expected to be greatly useful for developing materials or evaluating physical properties. Therefore, there is a need for a method for precisely evaluating molecular orbital information in a quantitative manner.

DISCLOSURE

Technical Problem

Accordingly, the present invention has been made keeping in mind the above problems occurring in the prior art, and an object of the present disclosure is to provide a method for precisely analyzing a molecular orbital in a quantitative manner, thereby enabling the development of novel materials.

Technical Solution

In accordance with an aspect thereof, the present disclosure addresses a method for analyzing a molecular orbital property, comprising: a) selecting a molecular orbital to be analyzed for molecular orbital distributions and computing molecular orbital distributions by a quantum chemistry calculation; b) building N blocks arranged in a radial direction from the center of the molecular structure; c) calculating a molecular orbital ratio (BX(k)) associated with each of the blocks; and d) rearranging the blocks consecutively by size of the orbital ratio (BX(k)).

In accordance with another aspect thereof, the present disclosure addresses a system for quantitatively analyzing molecular orbital properties, comprising: a) a first blocking module for selecting a molecular orbital to be analyzed for molecular orbital distributions, computing molecular orbital distributions by a quantum chemistry calculation, and building N blocks arranged in a radial direction from the center of the molecular structure; b) a data input module for calculating a molecular orbital ratio (BX(k)) associated with each of the blocks and inputting the calculated data; and c) a second blocking module for rearranging the blocks consecutively by size of the orbital ratio (BX(k)) to give a rearranged block spectrum.

Advantageous Effects

As described above, the method for analyzing molecular orbital properties in accordance with the present disclosure allows for the exact evaluation of molecular orbital properties in a quantitative manner by representing an entire molecular structure as an assembly of blocks and calculating molecular orbital ratios for individual blocks to give information on rearranged consecutive blocks. In addition, the method enables molecules to be compared to each other for similarity in molecular orbital, which is useful in developing novel materials for OLEDs (organic light-emitting diodes) or solar cells.

BEST MODE

Figure 1:
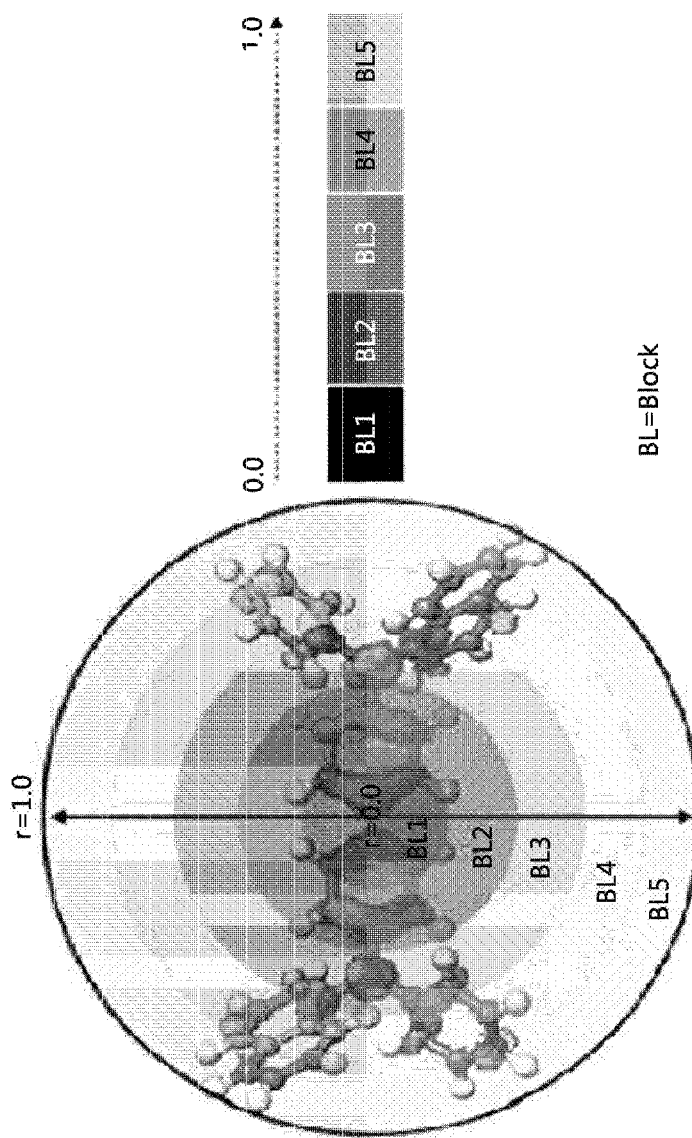
FIG. 1 shows a molecular orbital distribution of an NPB molecule used in OLED, divided into a total of 5 blocks (N=5) on the basis of distance from the center of the molecule in accordance with an embodiment of the present disclosure.
Figure 2:
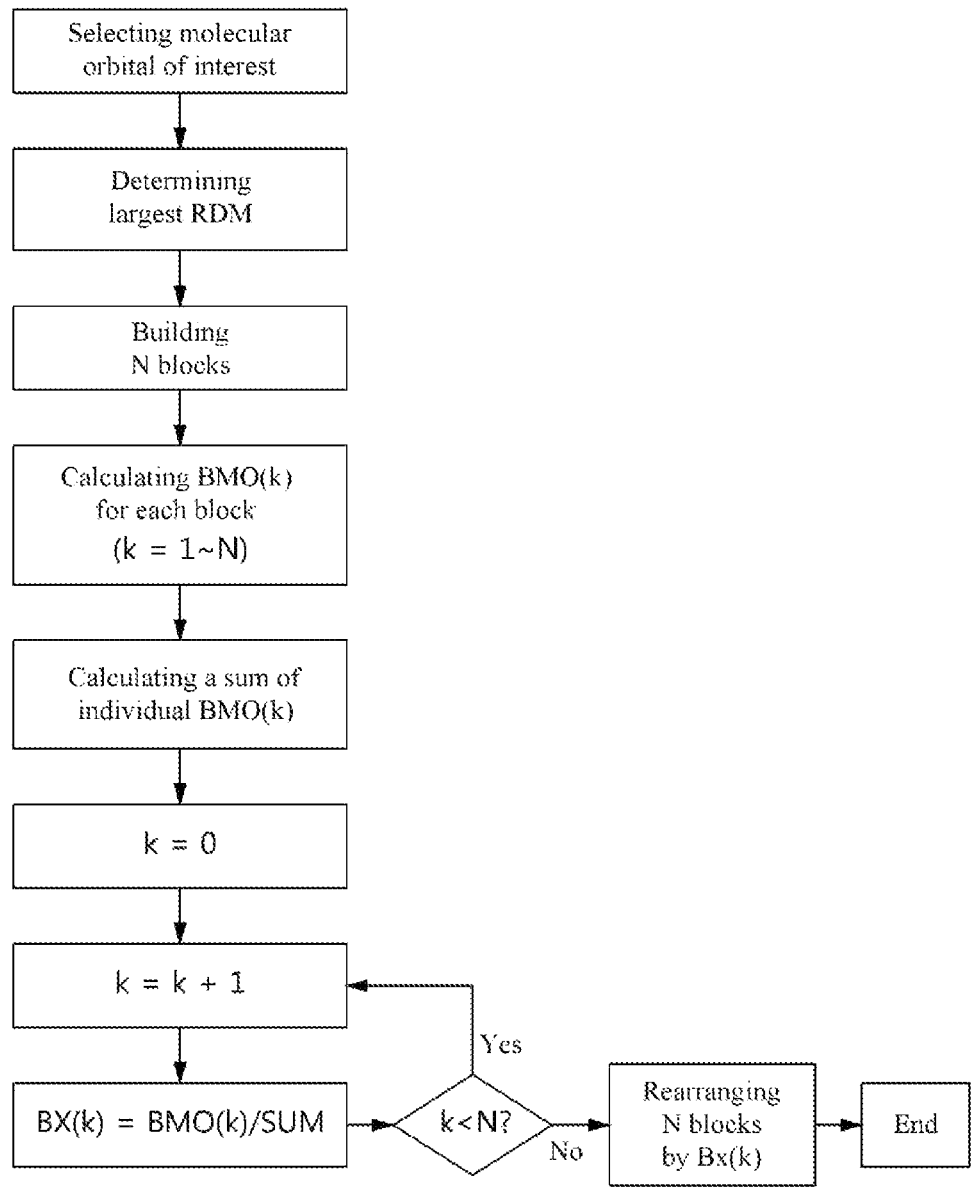
FIG. 2 is a flow chart illustrating a calculation procedure according to an AC2B (Assembly of Consecutive Building Block) according to the present disclosure.

Below, a detailed description will be given of the present invention.

In the present invention, a novel method is developed for analyzing molecular orbitals, and designated "AC2B (Assembly of Consecutive Building Block) method".

The AC2B (Assembly of Consecutive Building Block) method in accordance with the present disclosure is adapted to analyze a molecular orbital, and comprises: a) selecting a molecular orbital to be analyzed for molecular orbital distributions and computing molecular orbital distributions by a quantum chemistry calculation; b) building N blocks arranged in a radial direction from the center of the molecular structure; c) calculating a molecular orbital ratio (BX(k)) associated with each of the blocks; and d) rearranging the blocks consecutively by size of the orbital ratio (BX(k)).

In the AC2B of the present disclosure, the analysis of molecular orbital distribution is performed in such a manner that specific regions of an entire molecular structure are divided into blocks that are then arranged, followed by expressing the entire molecular structure with an assembly of the blocks.

In the method according to the present disclosure, a) a molecular orbital to be analyzed for molecular orbital distributions is selected and then computed for molecular orbital distributions by a quantum chemistry calculation; and b) N blocks are built in a radial direction from the center of the molecular structure.

In conjunction with the quantum chemistry calculation, a molecular orbital is defined as a mathematical function describing the wave-like behavior of an electron in a molecule. Regions in which molecular orbitals exist can be obtained by quantum-mechanical calculation. Any calculation method that takes advantage of quantum mechanics may be employed without limitations to obtain molecular orbital distributions. Preferable may be calculation through the distribution of the electron density function ($\psi 2$), which is a square of the orbital wave function ($\psi$) in each point determined in a molecular structure, or through single-point energy calculation or geometry optimization calculation. The present inventors calculated molecular orbital distributions using the program MATERIAL STUDIO DMol3 (ACCELRYS), which uses the Density Functional Theory (DFT), and depicted molecular orbital diagrams using the program VISUALIZER from MATERIAL STUDIO.

According to the present disclosure, the entire molecular structure of a molecule to be analyzed for molecular orbital properties is composed of an assembly of N consecutive blocks created in a radial direction from the center of the molecule over the entire molecular structure.

In this regard, the greatest RDM (Radially Discrete Mesh) that covers the entire molecular structure in a radial direction with a starting point at the center of the molecule (r=0.0) is calculated, and its size is designated r=1.0. RDM is a concept of confining the elemental atoms of a molecular structure within meshes arranged in a radial direction from the center of a molecule. In the molecular structure calculation through RDM, an intramolecular center ($x_c$, $y_c$, $z_c$) is obtained according to the following Mathematical Formulas 1-1 to 1-3.

$$x_C = \frac{1}{N^{Coord}} \sum_{k=1}^{N^{Coord}} x_K \quad \text{(Math Formula 1-1)}$$

$$y_C = \frac{1}{N^{Coord}} \sum_{k=1}^{N^{Coord}} y_K \quad \text{(Math Formula 1-2)}$$

$$z_C = \frac{1}{N^{Coord}} \sum_{k=1}^{N^{Coord}} z_K \quad \text{(Math Formula 1-3)}$$

wherein $N^{Coord}$ represents the total number of atomic coordinates constituting a molecule.

The total number of blocks, N, is not particularly limited, but preferably ranges from 3 to 100.

According to the molecular structure calculation by RDM, the entire molecular structure of a molecule of interest can be divided into blocks on the basis of distance from the center of the molecule.

This is elucidated with reference to FIG. 1. FIG. 1 shows a molecular orbital distribution of an NPB molecule, divided into a total of 5 blocks (N=5) on the basis of distance from the center of the molecule in accordance with an embodiment of the present disclosure. RDM covering the entire molecular structure is calculated, and then uniformly divided into 5 blocks BL1, BL2, BL3, BL4, and BL5. In FIG. 1, BL1 is the most proximal to the center of the molecule whereas BL5 is the outermost block. No particular limitations are imposed on sizes of the blocks. Preferably, the blocks are identical in size. The entire molecular structure can be expressed as an assembly of the blocks consecutively arranged in the order of BL1-BL2-BL3-BL4-BL5.

That is, in step b), the molecular orbital distribution of a molecule of interest is allowed to be expressed as consecutive blocks (AC2B, Assembly of Consecutive Building Block).

The present disclosure comprises c) calculating a molecular orbital ratio (BX(k)) associated with each of the blocks.

By the term "orbital ratio (BX(k)) associated with each of the blocks" is meant as an amount that a molecular orbital associated with a $k^{th}$ block occupies in comparison with the sum of entire molecular orbitals. The orbital ratio (BX(k)) associated with each of the blocks can be obtained by calculating individual molecular orbitals BMO(k)) associated with individual blocks, calculating a total sum of the entire molecular orbital from the individual molecular orbitals, and dividing the individual molecular orbitals BMO(k)) associated with each of the blocks by a total sum of the entire molecular orbital.

In step d), the blocks built in step b) are rearranged consecutively by size of the orbital ratio (BX(k)) to give a rearranged block spectrum (AC2B, Assembly of Consecutive Building Block). As used herein, the term "rearranged block spectrum" refers to AC2B (Assembly of Consecutive Building Block) obtained by rearranging the blocks built in step b) consecutively by the size of BX(k).

When the molecular orbital ratios calculated in step c) are in the order of BX(5)>BX(4)>BX(3)>BX(2)>BX(1), the blocks built in step b) are rearranged in the order of BL5-BL4-BL3-BL2-BL1. This rearranged block spectrum indicates that the molecular orbitals are distributed in a greatest amount in BL5, the most distal to the center of the molecule, and in a smallest amount in BL1, the most proximal to the center of the molecule.

According to the present disclosure, the rearranged block spectrum allows for exactly evaluating the distribution of molecular orbitals over the entire structure of a molecule in an intuitive manner.

Also, the present disclosure addresses a system for quantitatively analyzing molecular orbital properties using the method.

The system for quantitatively analyzing molecular orbital properties comprises: a) a first blocking module for selecting a molecular orbital to be analyzed for molecular orbital distributions, computing molecular orbital distributions by a quantum chemistry calculation, and building N blocks arranged in a radial direction from the center of the molecular structure; b) a data input module for calculating a molecular orbital ratio (BX(k)) associated with each of the blocks and inputting the calculated data; and c) a second blocking module for rearranging the blocks consecutively by size of the orbital ratio (BX(k)) to give a rearranged block spectrum.

The quantum chemistry calculation in the first blocking module may be performed through the distribution of the electron density function ($\psi2$), which is a square of the orbital wave function ($\psi$) in each point determined in a molecular structure, or through single-point energy calculation or geometry optimization calculation.

In the first blocking module, the blocks built to cover the entire molecular structure may be obtained using the RDM calculation method.

In the data input module, molecular orbital ratios (BX(k)) are input after they are obtained by calculating individual molecular orbitals BMO(k)) associated with individual blocks, calculating a total sum of the entire molecular orbital from the individual molecular orbitals, and dividing the individual molecular orbitals BMO(k)) associated with each of the blocks by a total sum of the entire molecular orbital.

MODE FOR INVENTION

Reference will now be made in detail to various embodiments of the present invention, specific examples of which are illustrated in the accompanying drawings and described below, since the embodiments of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims.

EXAMPLE

Figure 3A:
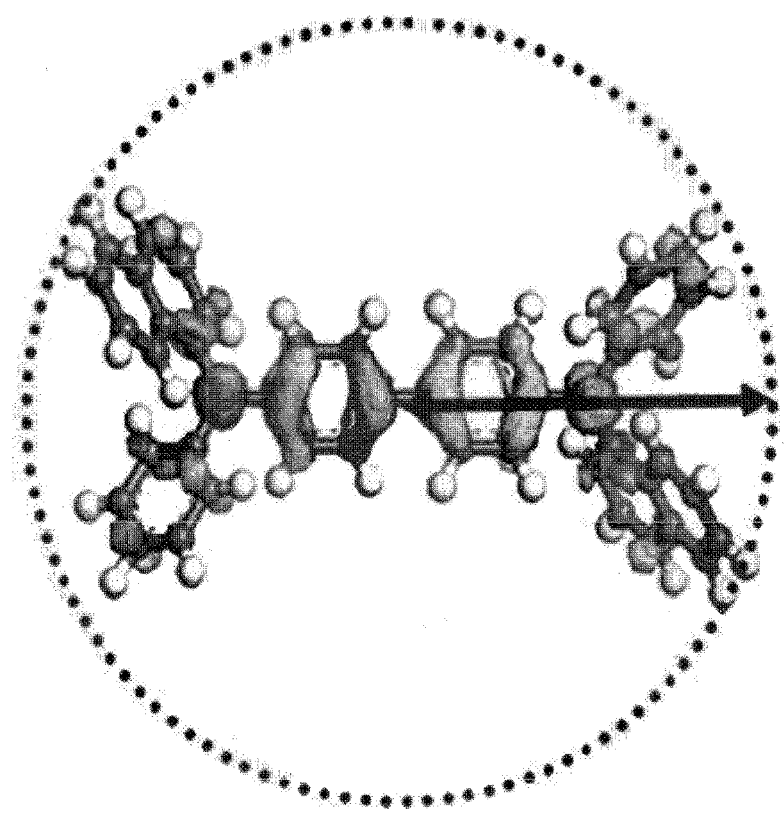
FIG. 3a is a diagram of molecular orbital distributions of NPB, visualized using the program VISUALIZER from MATERIAL STUDIO.

FIG. 3a is a diagram of molecular orbital distributions of NPB (N,N'-Di[(1-naphthyl)-N,N'-diphenyl]-1,1'-(biphenyl)-4,4'-diamine), visualized using the program VISUALIZER from MATERIAL STUDIO. In the diagram, the molecular orbital distribution is expressed as regions in which an electron is likely to exist (yellow/green regions). FIG. 3a shows an even molecular orbital distribution over the entire molecule. In comparison with this qualitative evaluation, the AC2B method according to the present disclosure can quantitatively analyze the molecular orbital properties of NPB by building consecutive blocks within which molecular orbital distributions of NPB are confined as follows.

Example 1

With regard to an NPB molecule in which molecular orbitals are distributed over the entire molecule, its molecular orbital properties were analyzed according to the method of the present disclosure.

Figure 3B:
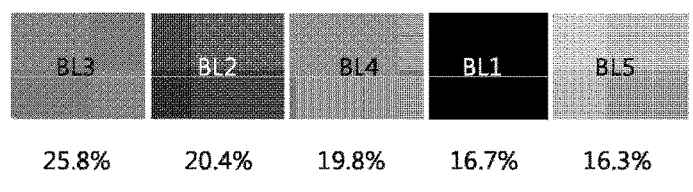
FIG. 3b is rearranged block spectra obtained by dividing each of entire molecular structures depicted in FIG. 3a into 5 blocks that are expanded from the center of the molecule, and then by rearranging the blocks by BX(k) size.

The entire molecular structure depicted in FIG. 3a was divided into 5 blocks that were expanded from the center of the molecule, and the blocks were rearranged by BX(k) size to give a rearranged block spectrum of BL3-BL2-BL4-BL1-BL5, as shown in FIG. 3b. Numerals below the rearranged individual blocks are values of BX(k). As can be seen in the rearranged block spectrum, the molecular orbital exists most abundantly in BL3, and $2^{nd}$ and $3^{rd}$ most abundantly in BL2 and BL3, respectively, while relatively small amounts of the molecular orbital are found in the most proximal block BL1 (most dark color) and the most distal block BL5 (most faint color). Hence, the molecular orbital is distributed over the entire molecular structure, with a higher concentration on the mean blocks (BL3, BL2, and BL4).

Example 2

With regard to an NPB molecule in which molecular orbitals are distributed mainly in peripheral regions distal to the center of the molecule, its molecular orbital properties were analyzed according to the method of the present disclosure.

The entire molecular structure was divided into 5 blocks that were expanded from the center of the molecule, and the blocks were rearranged by BX(k) size to give a rearranged block spectrum of BL4-BL5-BL3-BL2-BL1.

In the rearranged block spectrum, the molecular orbital was concentrated on the faintly colored blocks BL4 and BL5, distal to the center of the molecule, but was relatively sparse in the darkly colored blocks BL2 and BL1, proximal to the center of the molecule.

As such, the method of the present disclosure allows for the exact evaluation of molecular orbital properties in a quantitative manner by blocking an entire molecular structure to give a rearranged block spectrum or an assembly of consecutive building blocks.

The invention claimed is:

1. A method for analyzing a molecular orbital property of a target compound, comprising:
    a) selecting a molecular orbital of the target compound to be analyzed for molecular orbital distributions and computing molecular orbital distributions by a quantum chemistry calculation;
    b) building N blocks arranged in a radial direction from the center of the molecular structure;
    c) calculating a molecular orbital ratio (BX(k)) associated with each of the blocks; and
    d) rearranging the blocks consecutively by size of the orbital ratio (BX(k)) regarding the target compound, wherein the orbital ratio (BX(k)) associated with each of the blocks in step c) is obtained by calculating individual molecular orbitals BMO(k)) associated with individual blocks, calculating a total sum of the entire molecular orbital from the individual molecular orbitals, and dividing the individual molecular orbitals BMO(k)) associated with each of the blocks by a total sum of the entire molecular orbital.

2. The method of claim 1, wherein the quantum chemistry calculation of step a) is conducted through distribution of the electron density function ($\psi2$), which is a square of the orbital wave function ($\psi$), in each point determined with regard to a molecular structure.

3. The method of claim 1, wherein the quantum chemistry calculation of step a) is conducted through single-point energy calculation or geometry optimization calculation.

4. The method of claim 1, wherein the quantum chemistry calculation of step a) uses an RDM calculation method.

5. A system for quantitatively analyzing molecular orbital properties of a target compound, comprising:
  a) a first blocking module for selecting a molecular orbital of the target compound to be analyzed for molecular orbital distributions, computing molecular orbital distributions by a quantum chemistry calculation, and building N blocks arranged in a radial direction from the center of the molecular structure;
  b) a data input module for calculating a molecular orbital ratio (BX(k)) associated with each of the blocks and inputting the calculated data; and
  c) a second blocking module for rearranging the blocks consecutively by size of the orbital ratio (BX(k)) regarding the target compound to give a rearranged block spectrum,
  wherein the orbital ratio (BX(k)) associated with each of the blocks in the data input module is obtained by calculating individual molecular orbitals BMO(k)) associated with individual blocks, calculating a total sum of the entire molecular orbital from the individual molecular orbitals, and dividing the individual molecular orbitals BMO(k)) associated with each of the blocks by a total sum of the entire molecular orbital.

6. The system of claim 5, wherein the quantum chemistry calculation of the first blocking module is conducted through distribution of the electron density function ($\psi 2$), which is a square of the orbital wave function ($\psi$), in each point determined with regard to a molecular structure.

7. The system of claim 5, wherein the quantum chemistry calculation of the first blocking module is conducted through single-point energy calculation or geometry optimization calculation.

8. The system of claim 5, wherein the quantum chemistry calculation of the first blocking module uses an RDM calculation method.

* * * * *